United States Patent [19]

Parisi

[11] Patent Number: 4,861,332
[45] Date of Patent: Aug. 29, 1989

[54] ULTRASONIC PROBE

[75] Inventor: Tulio T. Parisi, San Diego, Calif.

[73] Assignee: Ultramed Corporation

[21] Appl. No.: 935,396

[22] Filed: Nov. 26, 1986

Related U.S. Application Data

[63] Continuation-in-part of Ser. No. 851,220, Apr. 14, 1986, abandoned.

[51] Int. Cl.$^4$ ............................................. A61B 17/20
[52] U.S. Cl. .................................. 604/22; 128/24 A; 128/305; 604/27; 604/35
[58] Field of Search ....................... 604/22, 27, 30–35, 604/43–45, 118, 119, 902; 128/24 A, 303 R, 305, 328; 433/118, 119; 310/325

[56] References Cited

U.S. PATENT DOCUMENTS

| | | | |
|---|---|---|---|
| 2,498,737 | 2/1950 | Holden | 128/24 A |
| 2,787,833 | 4/1957 | Reineke | 433/119 |
| 3,371,660 | 3/1968 | Carlin | 128/24 A |
| 3,589,363 | 6/1971 | Banko et al. | 604/22 |
| 3,645,255 | 2/1972 | Robinson | 128/24 A |
| 3,772,538 | 11/1973 | Supitilov | 310/325 |
| 3,809,977 | 5/1974 | Balamuth et al. | 128/24 A |
| 4,169,984 | 10/1979 | Parisi | 128/305 |
| 4,320,761 | 3/1982 | Haddad | 604/284 |
| 4,561,438 | 12/1985 | Bonnet et al. | 128/24 A |
| 4,660,573 | 4/1987 | Brumbach | 128/303 R |

FOREIGN PATENT DOCUMENTS 0731962  5/1980  U.S.S.R. ............... 128/24 A

Primary Examiner—C. Fred Rosenbaum
Assistant Examiner—Mario Costantino
Attorney, Agent, or Firm—Nydegger & Harshman

[57] ABSTRACT

A transducer in a probe is positioned between first and second body members in a housing. An elongated tip is coupled to the first body member. A mass is provided on the first body member to amplify the ultrasonic vibrations imparted to the tip by the transducer. A tube extends through the second body member and the transducer into the first body member to hold the transducer in an abutting relationship with the body members without extending any bolts between the body members and the transducer. The tube, the body member, the transducer and the tip have axial passage which provide an axial aspiration path from the free end of the tip. Suction in the passageways exhausts through the passageways material removed from a particular area in a patient's body upon the application of the tip to the particular area while the tip is vibrating ultrasonically. A coil spring within the housing prestresses the transducer by compressing the transducer between the body members and also acts to amplify the ultrasonic vibrations imparted to the tip by the transducer. The probe is driven by applying an alternating electric voltage across the transducer. The probe may include an irrigation system parallel to the passage in the probe tip.

15 Claims, 3 Drawing Sheets

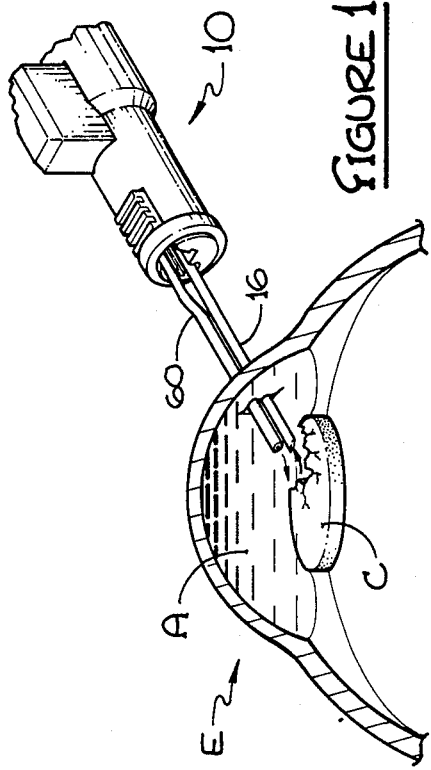
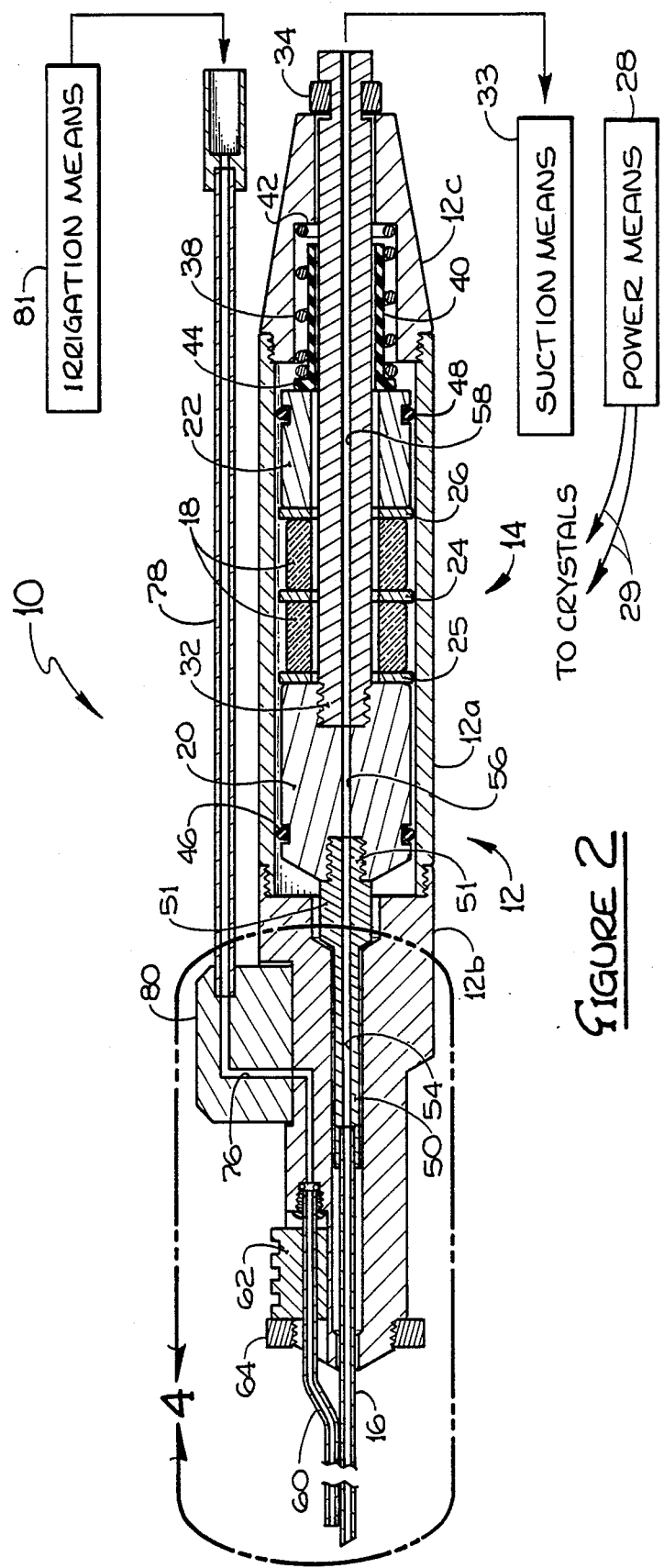

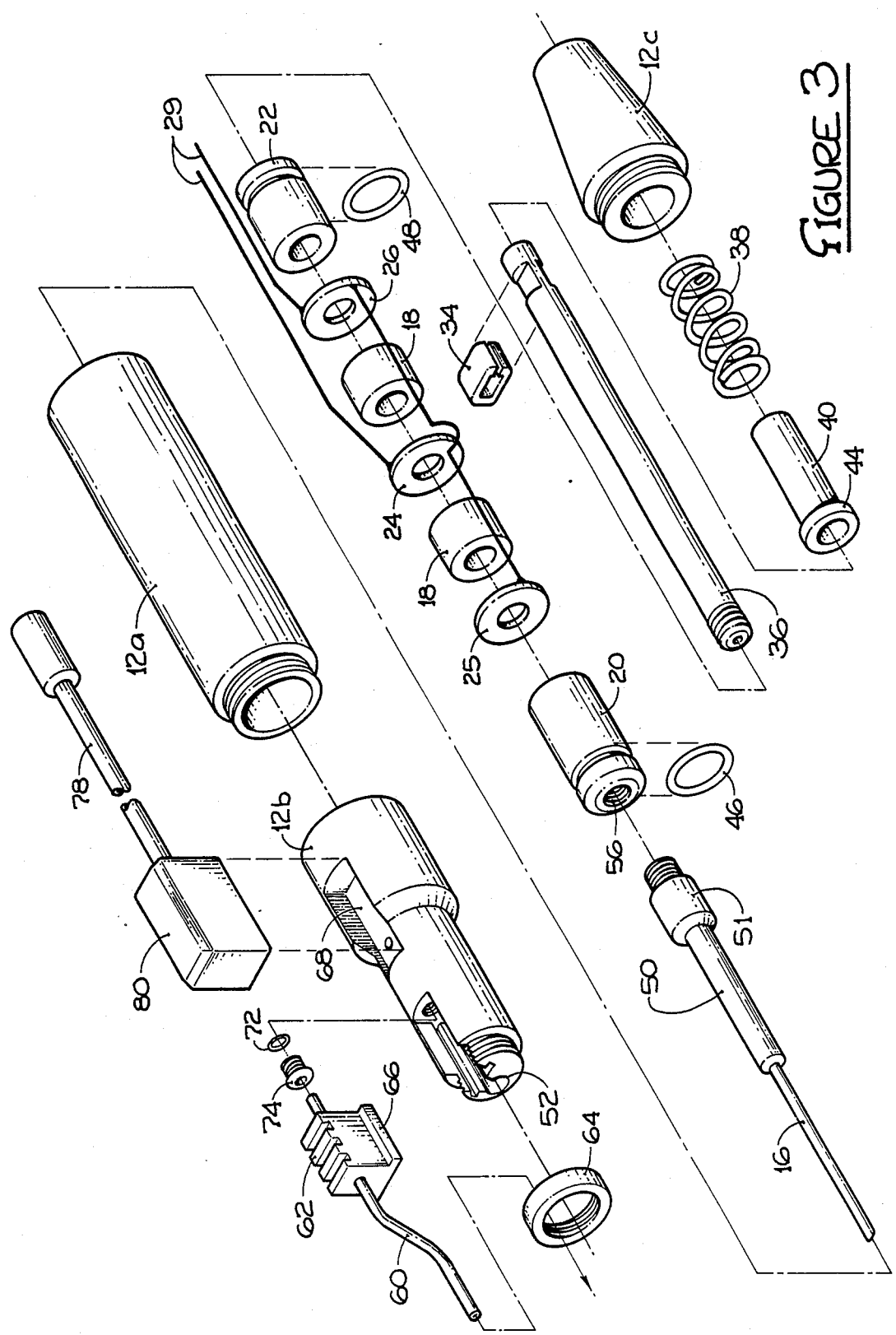

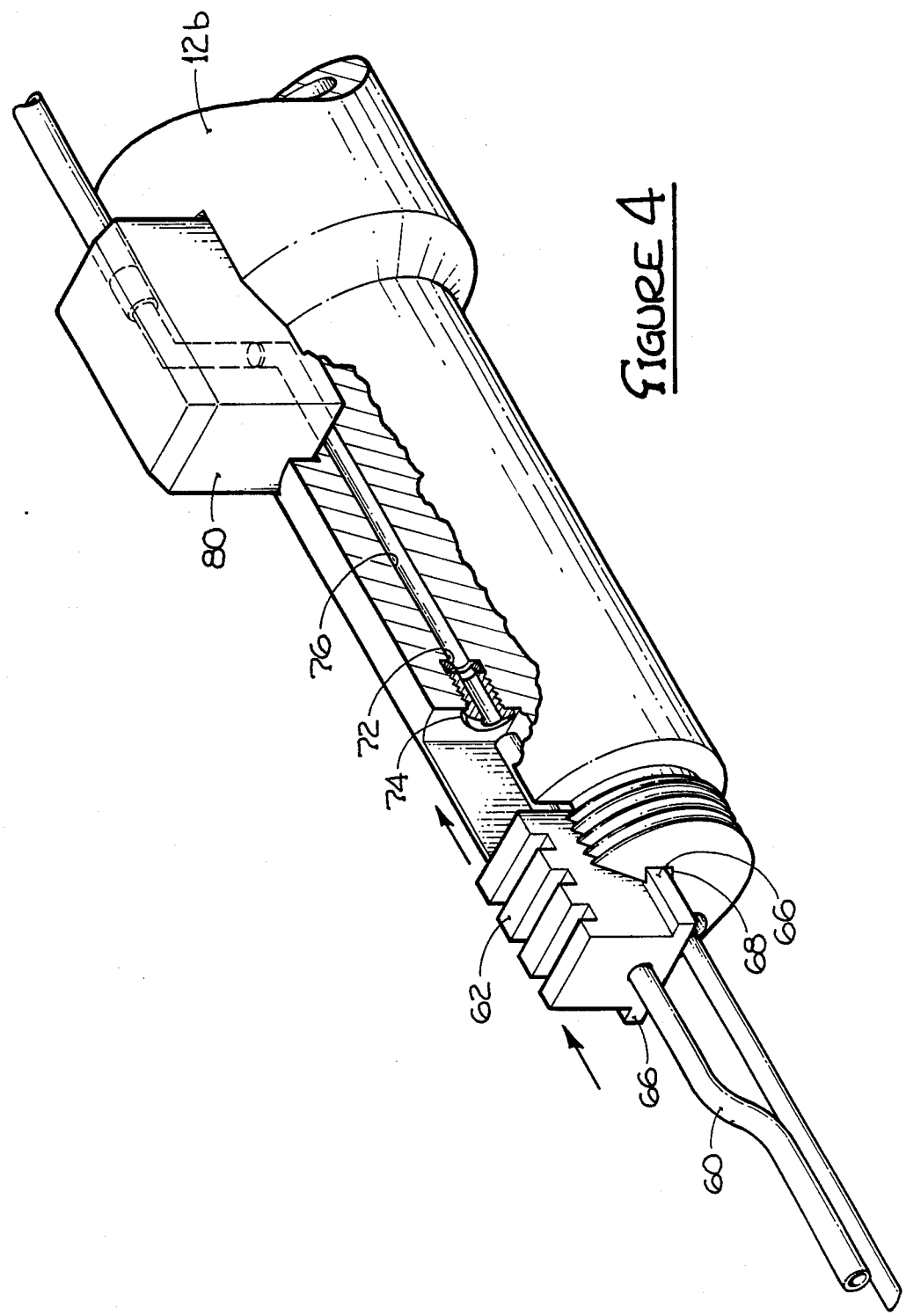

ULTRASONIC PROBE

This application is a continuation-in-part of application Ser. No. 851,220 filed by me on Apr. 14, 1986 now abandoned and assigned of record to the assignee of record of this application.

TECHNICAL FIELD

The present invention pertains generally to an ultrasonic probe, and more particularly, to an improved ultrasonic probe which more efficiently emulsifies and removes tissue by aspiration through the tip of the probe.

BACKGROUND OF THE INVENTION

Until the late 1960's ophthalmological surgical techniques for cataract removal were performed by using standard intracapular cataract extraction techniques which, although generally satisfactory, require a prolonged recovery time as long as several months. Since that time, a procedure known as phacoemulsification, or use of an ultrasonic probe to break up and remove cataracts, has become widely used because it offers a remarkable decrease in recovery time. Indeed, a patient can sometimes return to work the day after surgery with this technique.

The procedure for removal of cataract tissue is described in an article entitled "History of Emulsification and Aspiration of Senile Cataracts," by Charles D. Kelman and appearing in Transaction of American Academy of Opthalmology and Otoaryngology, volume 78, January-February, 1974, pages OP5-13 (originally presented at the 78th Annual Meeting of the American Academy of Ophthalmology and Otoaryngology, Dallas, Texas, Sept. 16-20, 1973).

Generally speaking, a tip in the form of a hollow tube is inserted into the anterior chamber of the eye, through a small incision, into contact with the cataract tissue. The tip is vibrated by a hand-held probe at an ultrasonic rate, and hydrodynamic flow of a saline solution is established in order to prevent collapse of the anterior chamber. As particles of the cataract tissue are cut from the cataract mask, the particles are suspended in the saline solution and removed from the chamber through the tip of the ultrasonic probe by vacuum aspiration. In the case of hard cataracts, those particles with a tendency to slide into contact with the walls of the chamber have an abrasive character. Since certain portions of the eye including the chamber walls are prone to abrasion sensitivity, the cataract particles must be quickly, and as possible, removed from the chamber. This is done by aspiration through the hollow tip of the ultrasonic probe.

During aspiration of cataract tissue, the tip of the ultrasonic probe must be very carefully manipulated under the field of a microscope in order to prevent aspirating other than cataract tissue and to ensure that all the cataract particles are removed from the chamber. Close control of the tip is especially critical at the peripheral regions of the cataract.

The tip must be able to effectively remove the cataract tissue without clogging or otherwise hindering the surgical procedure. Several improved ultrasonic probes have been developed for performing this and other delicate types of surgery as well as cleaning teeth and the like. These probes generally consist of a tip for cutting/cleaning material at the operation site, a handpiece for mounting the tip and associated circuitry, and a piezoelectric crystal or other means for supplying ultrasonic energy to vibrate the tip. My prior design disclosed in U.S. Pat. 4,169,984, is one such improved ultrasonic probe.

Despite the improvements that have been made, the prior ultrasonic probes have not proved to be as effective and efficient in removing the undesired tissue as they could be. As indicated above, the probe must first and foremost efficiently remove the undesired tissue from the surgical field. The vacuum lines of the prior art devices are often tortuous, adversely affecting the efficiency with which particles are aspirated. If clogging occurs, the surgery must be halted to clear the clogging or to change equipment. The delay in surgery increases the trauma and risk to the patient.

Piezoelectric crystal transducers have been commonly used to provide the ultrasonic vibrations of the probe tip. These piezoelectric crystals have been compression loaded as a protective measure since they have a tendency to break from shock loading and dynamic fatigue. In the past, the compression loading has obtained by positioning the crystal transducers between two elements which have been bolted together, applying compression to the crystal transducers. With this design, it is difficult to apply compression loading uniformly across the transducer surface, and breakage can occur either during mounting or in operation due to localized stresses. Also, the clamping bolts may be affected by thermal expansion and contraction from heating and cooling during probe operation. This changes the compression loading on the crystals, thus causing a shift in resonant frequency. Such a shift in resonant frequency directly affects probe cutting action. Avoiding any such fluctuations in cutting action is particularly critical to patient safety where, for example, the surgeon is cutting the peripheral regions of the cataract means.

Further, the previous ultrasonic probes that incorporating irrigation mechanisms with the aspiration elements have tended to be large and cumbersome and inefficient in the performance of th delicate surgery. The irrigation stream has tended to be misdirected, failing to provide most effective results. Irrigation streams provided by prior art devices have typically interfered with the surgeon's view of the ultrasonic tip/tissue interface.

A new and improved ultrasonic probe having (1) a substantially straight-through aspiration path, (2) irrigation and aspiration mechanisms contained in a small maneuverable housing, and (3) piezoelectric transducers continuously and uniformly loaded in compression is, therefore, needed.

SUMMARY OF THE INVENTION

Accordingly, it is a primary object of the present invention to provide a new and improved probe for ultrasonically removing tissue.

Another object of the invention is to provide a new and improved ultrasonic probe that is smaller, lighter, and easier to use and to disassemble for service than the ultrasonic probes of the prior art.

Another object of the invention is to provide a new and improved ultrasonic probe with resilient uniform compression loading across the transducer assembly for efficient, consistent and reliable operation.

Another object of the invention is to provide a new and improved probe with a substantially straight vacuum line for efficient aspiration of the removed tissue.

Another object of the invention is to provide a new and improved ultrasonic probe having an irrigation system parallel to the operative tip for effective and efficient irrigation of the surgical field.

A further object is to provide an ultrasonic probe in which the ultrasonic movements of the probe tip are amplied above those provided by the transducer.

Additional objects, advantages, and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention as described herein, an improved ultrasonic probe is provided. The probe may be used, for example, to remove cataract tissue from the eye or fatty tissue from the body of a human being or other animal. The ultrasonic probe comprises an elongated operative tip releasably connected to a piezoelectric transducer asembly contained within a handpiece or housing. The transducer assembly is prestressed between a pair of body members slidably received in the housing by a compression spring. The compression spring acts on a cooperative basis with the transducer assembly to amplify the vibrations imported to the tip by the transducer assembly. The operative tip is connected to the transducer assembly through the first of the body members. The body member is provided with a mass at a position near the tip to amplify the ultrasonic vibrations imparted to the tip by the transducer assembly.

The piezoelectric transducer assembly may comprise first and second piezoelectric crystals. The crystals and body member include respective axial bores all in alignment. A connecting tube extends partially through the axial bore of the first body member and completely through the respective axial bores of the piezoelectric crystals and the second body member. One end of the connecting tube securely engages threads formed in the axial bore of the first body member. The second, opposite end of the connecting tube is secured by a clip which abuts the exterior of the housing. Thus, the connecting tube serves to interconnect the piezoelectric crystals and the body members and maintain them in alignment and under compression.

The operative tip extends through the housing and is securely connected to the end of the first body member opposite the connection to the connecting tube. The operative tip includes an inner passage for aspiration of tissue material to be cut and removed from the body. The inner passage is aligned and communicates with the axial bore of the first body member and the connecting tube so as to provide a substantially straight-through aspiration path of improved efficiency.

The housing is formed of a molded material, such as ABS plastic, and comprises a central, cylindrical member and a pair of end members. Each end member is threaded to engage with threads on the respective end of the central member.

A removable irrigation tube is connected to the front end member of the housing by means of a retainer base and collar. The irrigation tube extends from the housing parallel to the operative tip for optimum positioning of the irrigation stream during surgery. Proper alignment of the retainer base on the housing is assured by guide rails which are provided on the retainer base and which are received in a slot in the housing. The irrigation tube communicates with a feed line which is releasably secured to the housing by means of a mounting block.

A high frequency alternating voltage for energizing the piezoelectric crystals of the transducer assembly is applied across the crystals by disc electrodes located between and at each end of the crystals. The application of the alternating voltage across the crystals causes the transducer assembly to vibrate at an ultrasonic frequency. These vibrations are mechanically coupled to the operative tip through the first body member. To assure proper control of the handpiece by the surgeon, the body members and transducer assembly are insulated mechanically and electrically from the housing by a pair of insulators, such as O-rings.

The ultrasonic vibrations of the operative tip are used to break up and remove the undesired cataract or fatty tissue from the body. The undesired tissue material is aspirated through the operative tip, first body member and connecting tube. The parallel irrigation tube supplies a saline solution to wash the surgical field and, for example, prevent collapse of the anterior chamber of the eye during cataract removal.

Still other objects of the present invention will become readily apparent to those skilled in the art from the following description wherein there is shown and described a preferred embodiment of this invention, simply by way of illustration of one of the modes best suited to carry out the invention. As will be realized, the invention is capable of other different embodiments, and its several details are capable of modifications in various, obvious aspects all without departing form the invention. Accordingly, the drawings and descriptions will be regarded as illustrative in nature and not as restrictive.

BRIEF DESCRIPTION OF THE DRAWINGS

The accompanying drawings incorporated in and forming a part of the specification illustrate several aspects of the present invention and together with the description serves to explain the principles of the invention. In the drawings:

FIG. 1 is a perspective view of a cataract pulverization operation utilizing the ultrasonic probe of the present invention;

FIG. 2 is a cross-sectional side view of the probe;

FIG. 3 is an exploded view of the probe; and

FIG. 4 is a detailed and enlarged perspective view of the irrigation tube assembly, with certain parts being at least partially broken away to show other parts in additional detail.

Reference will now be made in detail to the present preferred embodiment of the invention, as example of which is illustrated in the accompanying drawings.

DETAILED DESCRIPTION OF THE DRAWINGS

Reference is now made to FIG. 1–4, and initially to FIG. 2 showing an improved ultrasonic probe, generally indicated at 10, in cross-section. The probe 10 is used for ultrasonically removing tissue and comprises a housing generally indicated at 12 and containing a piezoelectric transducer assembly, generally indicated at 14, for imparting ultrasonic vibrations to an elongated operative tip 16. The housing 12 includes a central cylindrical member 12a and a pair of end members 12b and 12c.

Referring to FIGS. 2 and 3, the power means includes piezoelectric transducer assembly 14 with first and second piezoelectric crystals 18 located within housing 12 between first body member 20 and second body member 22. The piezoelectric crystals 18 are powered through disc electrodes 24–26 connected to a high frequency source of power means 28 of alternating current by lead wires 29 (see FIG. 3 also). The disc electrode 24 is positioned between the crystals 18 while the electrodes 25, 26 are positioned between the crystals and the body members 20, 22, respectively.

A connecting tube 30 extends through axial bores in the crystals 18, body members 20 and 22 and electrodes 24–26 to maintain these components in axial alignment within the housing 12. A forward end of the connecting tube 30 includes threads 32 that engage threads in the axial bore of the first body member 20 for secure connection. The rear end of the tube 30 extends through the end member 12c of the housing 12 for connection to a suction source 33. A clip 34 received in detent 36 in connecting tube 30 abuts the end member 12c and allows the prestressing of the crystals 18 as discussed in further detail below.

A coil spring 38 provides resilient compression to the crystals 18 so as to assure consistent and reliable operation of the probe under all operating conditions. The spring 38 is disposed around and carried on a guide sleeve 40 that maintains the spring in proper position within the end member 12c of the housing 12. The coil spring 38 is compressed between wall 42 of end member 12c and the collar 44 of guide sleeve 40. The coil spring 38 also acts to store energy during the vibratory movement of the piezoelectric crystals toward the right in FIG. 3 and to urge the crytals toward the left in FIG. 2 when the crystals start to vibrate toward the left in FIG. 2. This tends to amplify the ultrasonic vibrations imparted to the tip 16 by the crystals 18. Since the connecting tube 30 is secured to the first body member 20 by threads 32 and anchored adjacent its distal end by the clip 34 abutting the end member 12c, it should be appreciated that the crystals 18 are prestressed between the body members 20, 22.

The force thus generated by the coil spring 38 provides a constant and uniform loading across the crystals 18, substantially eliminating localized stresses that can result in crystal breakage. Further, the resilient nature of the compression provided to the crystals 18 by the spring 38 dramatically increases electromechanical coupling over the rigid nature of the compression provided by the bolting together of the crystals as done in the prior art. The probe 10 of the present invention is therefore more efficient than the probes of the prior art, allowing effective operation at a lower voltage with reduced dielectric losses. Thus, the probe operates at a lower overall temperature than the probes of the prior art, thereby reducing cooling requirements and improving reliability.

The body members 20, 22 are electrically and mechanically insulated from housing 12 by O-rings 46, 48. The O-rings 46, 48 float the body members 20, 22 within the housing 12 so that the ultrasonic vibration is not coupled to the housing, thereby permitting precise control by the operator.

An alternating voltage is applied across the piezoelectric transducers 18 between the disc electrodes 24, 25 and 24, 26 causing piezoelectric crystals 18 to vibrate at an ultrasonic frequency. Ultrasonic vibrations from the crystals 18 are imparted to the operative tip 16 by mechanical coupling through the disc electrode 25, first body member 20 and enlarged tip base 50.

A portion of the operative tip including the tip base 50 is contained within the housing 12. The tip base 50 has and increased mass 51 at one end. The mass 51 stores energy and uses this energy as a hammer to increase the force imposed upon the tip 16 when the tip is moved to the left in FIG. 2 by the crystal transducers 18. In this way, the mass 51 acts to amplify the ultrasonic vibrations imparted to the tip 16.

The remaining portion of operative tip 16 extends beyond the housing 12 through aperture 52 of end housing member 12b. The operative tip 16 contains an inner passageway 54 for aspiration of removed material. The inner pasageway 54 is aligned and communicates with the axial bore 56 of the first body member 20 and the inner passage 58 of connecting tube 30 to form a substantially straight-through aspiration path.

Referring to FIGS. 2–4, and most specifically to FIG. 4, an irrigation tube 60 is releasable connected through a retainer base 62 by a collar 64 to end housing member 12b. Retainer base 62 has guide rails 66 which are received in a slot 68 of end housing member 12b to assure properly aligned connection of the irrigation tube 60 parallel to operative tip 16 during assembly (note action arrow).

Irrigation tube 60 engages O-ring 72 upon insertion through an insert 74 of end housing member 12b to communicate with feed passage 76. A feed line 78 is secured to end housing member 12b with a mounting block 80. The feed line 78 is connected to an irrigation means 81. When properly connected, irrigation solution is fed through feed line 78 into feed passage 76 is end member 12b to irrigation tube 60 for discharge into the surgery field.

Referring now to FIG. 1, a procedure is shown for removing cataract tissue from an eye by using the ultrasonic probe 10 in accordance with the invention. A small incision of approximately 3 mm is made to reach the anterior chamber A of the eye E to gain access to cataract C. Operative tip 16 and irrigation tube 60 of ultrasonic probe 10 are inserted through the incision into the anterior chamber A. The flow of liquid through irrigation tube 60 is begun and then the surgeon activates vibration of the operative tip 16. The operative tip 16 vibrates at an ultrasonic frequency and pulverizes the hardened cataract C. The pulverized particles are suspended in the liquid supplied by the irrigation tube 60 and aspirated through the inner pasages 54, 56, 58 of the operative tip 16, the first body member 20 and connecting tube 30, respectively, to the suction source 33. The fluid provided by irrigation tube 60 also serves to maintain the equilibrium in the anterior chamber A to prevent collapse of the chamber during the operative procedure.

In summary, the ultrasonic probe 10 of the present invention, having uniform and constant prestress compression loading of the piezoelectric transducer 18 and having parallel irrigation with the substantially straight-through aspiration through the operative tip 16, provides significant advantages over the prior art ultrasonic probes. The resilient compression coil spring 64 provides uniform compression loading which avoids breakage of the transducers during mounting, due to localized stresses, during mounting or operation of the transducers. Enhanced electromechanical coupling is also provided for improved operating efficiency at lower temperatures. The spring 64 also acts to amplify the ultrasonic vibrations of the tip 16. The mass 51 on the base 50 also acts to amplify the ultrasonic vibrations of the tip 16.

The parallel irrigation tube 60 secured to the housing 12 provides irrigation of the operative region, thereby eliminating the need of manipulating an extra instrument. The straight aspiration path of the ultrasonic probe 20 through the tip 16 and connecting tube 30 provides substantially clog-free aspiration. The fixed positioning by the tube 30 of the crystal transducers 18 between the body members 20 and 22 without any attachment of the crystals to the body members also facilitates an optimal operation of the probe by applying a substantially uniform loading across the transducer surfaces..

The foregoing description of a preferred embodiment of the invention has been presented for purposes of illustration and description. It is not intended to be exhaustive or to limit the invention to the precise form disclosed. Obviously, many modifications and variations of the present invention are possible in light of the above teachings. The embodiment has been chosen and described to provide the best illustration of the principles of the invention and its practical application to thereby enable one of ordinary skill in the art to utilize the invention in various modifications as are suited to the particular use contemplated. It is intended that the scope of the invention be defined by the claims appended hereto.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

I claim:

1. An ultrasonic probe for removing and aspirating material, comprising:
    a housing;
    compressible piezoelectric transducer means disposed within said housing and energizable to provide ultrasonic vibrations, said transducer means having an axial bore;
    power means for energizing said transducer means, said power means having a first and a second body member formed with axial bores, said body members disposed in said housing on opposite sides of said transducer means with said axial bores of said transducer means and said first and second body members substantially in alignment with one another;
    an operative tip connected to said power means for ultrasonic vibration by the power means, said operative tip having an inner passage for the aspiration of material, said inner passage being aligned, and communicating with, said axial bore in said first body member when said tip is connected to said first body member;
    a coil spring disposed in said housing for compressing and transducer means to prestress said transducer means,
    a connecting tube extended through respective axial bores of said transducer means and said second body member and at least partially through said first body member in communication with said inner passage of said operative tip; and
    a guide sleeve disposed on said connecting tube, said coil spring provided within said housing and disposed on said guide sleeve,
    the power means, the operative tip and the coil spring being disposed in a coaxial relationship, the coil spring means being disposed against the power means only at the end removed from the tip to amplify the ultrasonic movements of the tip in the direction away from the housing.

2. The ultrasonic probe set forth in claim 1, wherein said connecting tube is securely connected to said first body member.

3. The ultrasonic probe set forth in claim 1, wherein said guide sleeve has a collar and the collar is disposed adjacent the second body member and said coil spring presses said collar of said guide sleeve against said second body member to compress said body members and transducer means relative to one another.

4. The ultrasonic probe set forth in claim 1, wherein said power means includes means for applying an alternating electronic voltage across said transducer means.

5. The ultrasonic probe set forth in claim 1, further comprising:
    irrigation means for infusing fluid to the operative region of said tip, said irrigation means being disposed on said housing in a substantially parallel relationship with the power means, the operative tip and the coil spring.

6. The ultrasonic probe set forth in claim 5, wherein said irrigation means provides irrigating fluid in a direction parallel to said operative tip.

7. The ultrasonic probe set forth in claim 6, wherein a retainer base and a collar are supported on the housing and
    said irrigation means includes a removable irrigation tube connected to said retainer base and said collar.

8. The ultrasonic probe set forth in claim 7, wherein said retainer base includes a guide rail and said housing includes a slot for receipt of said guide rail, said slot and said guide rail providing connection of said irrigation tube to said housing in an aligned relationship with the operative tip.

9. The ultrasonic probe set forth in claim 5, wherein a mounting is disposed on the housing and
    said irrigation means includes a feed line having a mounting block for releasably securing said feed line to said housing.

10. An ultrasonic probe for removing and aspirating material, comprising:
    a housing;
    transducer means disposed in said housing for providing ultrasonic vibrations when energized, said transducer means including a first and a second piezoelectric transducer with axial bores;
    power means for energizing said transducer means to obtain ultrasonic vibrations from said transducer means, said power means includes washer electrodes;
    first and second body members disposed within said housing on opposite sides of said transducer means and in axial alignment with said transducer means, said body members including respective axial bores aligned with said axial bore of said transducer means, said washer electrodes provided between said transducer means and said first and second body members;

an elongated operative tip disposed in axial alignment with the transducer means and the first and second body members and including means for engaging said first body member and further including an inner passage for material aspiration;

a connecting tube extending through said axial bores of said transducer means and said axial bore of said second body member and partially through said first body member, said connecting tube having an axial bore communicating with said inner passage of said operative tip and said connecting tube interconnecting said body members resilient compression means disposed in said housing for compressing said transducer means between said body members to prestress said transducer means; and a guide sleeve positioned on said connecting tube and supporting said resilient compression means.

11. The ultrasonic probe set forth in claim 10 further including irrigation means disposed on the housing in substantially parallel relationship with the operative tip for providing a stream of irrigation fluid in a direction substantially parallel to said operative tip.

12. The ultrasonic probe set forth in claim 11, wherein
a retainer base and a collar are disposed on the housing and
said irrigation means includes a removeable irrigation tube connected to said retainer base and collar.

13. The ultrasonic probe set forth in claim 12, wherein
said retainer base includes a guide rail and said housing includes a slot for receiving said guide rail, said guide rail and slot providing for connection of said irrigation tube to said housing in an aligned relationship with the operative tip.

14. The ultrasonic probe set forth in claim 10, wherein
a first end of said connecting tube is secured to said first body member and an opposite end of said connecting tube is secured behind said guide sleeve for attachment to a vacuum means.

15. The ultrasonic probe set forth in claim 14, wherein
the means for securing said opposite end of said connecting tube includes a clip received in a detent in said tube, said clip abutting an end of said housing.

* * * * *